United States Patent [19]

Orr

[11] Patent Number: 4,853,214
[45] Date of Patent: Aug. 1, 1989

[54] ANTIPERSPIRANT CREAMS CONTAINING VOLATILE SILICONES

[75] Inventor: Thomas V. Orr, Cincinnati, Ohio

[73] Assignee: The Procter & Gamble Company, Cincinnati, Ohio

[21] Appl. No.: 93,928

[22] Filed: Sep. 8, 1987

[51] Int. Cl.$^4$ ............................................. A61K 7/035
[52] U.S. Cl. .................................... 424/69; 424/66; 424/67; 424/68
[58] Field of Search ................. 424/69, 66, 67, 68

[56] References Cited

U.S. PATENT DOCUMENTS

| | | | |
|---|---|---|---|
| 4,053,581 | 10/1977 | Pader et al. | 424/68 |
| 4,083,956 | 4/1978 | Shelton | 424/66 |
| 4,268,499 | 5/1981 | Keil | 424/68 |
| 4,278,655 | 7/1981 | Elmi | 424/47 |
| 4,350,605 | 9/1982 | Hughett | 252/305 |
| 4,526,780 | 7/1985 | Marschner | 424/65 |
| 4,551,330 | 11/1985 | Wagman et al. | 424/59 |

FOREIGN PATENT DOCUMENTS

| | | | |
|---|---|---|---|
| 0028853 | 6/1980 | European Pat. Off. | 424/66 |
| 28853 | 5/1981 | European Pat. Off. | |
| 135315 | 3/1985 | European Pat. Off. | |
| 6117410 | 5/1984 | Japan . | |
| 1083109 | 8/1984 | Japan | 424/63 |
| 2096891 | 3/1982 | United Kingdom . | |

Primary Examiner—Thurman K. Page
Assistant Examiner—Penny L. Prater
Attorney, Agent, or Firm—David K. Dabbiere; Douglas C. Mohl; Steven J. Goldstein

[57] ABSTRACT

Antiperspirant cream compositions, comprising:
(a) from about 5% to about 60% of a volatile silicone oil
(b) from about 0.1% to about 60% of a non-volatile emollient having a viscosity of at least about 10 cs at 25° C.;
(c) from about 2% to about 10% of a particulate thickening material; and
(d) from about 15% to about 45% of a particulate antiperspirant active material; and
(e) from about 0.1% to about 10% of a particulate cellulose ether polymer, wherein the compositions have penetration force values of from about 150 grams to about 800 grams at 25° C. and at 50% relative humidity. These compositions preferably contain a cosmetic powder material, at a level of from about 2% to about 20%. This invention also provides methods for making these compositions.

24 Claims, No Drawings

ANTIPERSPIRANT CREAMS CONTAINING VOLATILE SILICONES

BACKGROUND OF THE INVENTION

The present invention relates to cosmetic cream compositions containing an antiperspirant active material. In particular, it relates to antiperspirant creams, and methods for making such compositions, with improved stability, efficacy, cosmetic and wash-off characteristics.

Compositions designed to stop or reduce the flow of perspiration are well known in the cosmetic and chemical literature. Antiperspirants typically contain an astringent material, such as an astringent aluminum or zirconium salt. These compositions are designed to deliver the active to the skin in an effective form, while being cosmetically acceptable.

A variety of methods have been used to apply antiperspirant compositions to the skin. For example, sprays, roll-ons, creams and stick compositions are commonly used. Such formulations are described in S. Plechner, "Antiperspirants and Deodorants" 2 *Cosmetics, Science and Technology* 373-416 (M. Balsam and E. Sagarin, editors, 1972).

Cream emulsions are also described, for example, in U.S. Pat. No. 4,268,499, Keil, issued May 19, 1981, and Australian patent specification No. 8,430,026, published Jan. 3, 1985. Anhydrous creams, in gel form, are described, for example, in U.S. Pat. No. 4,083,956, Shelton, issued Apr. 11, 1978, and European patent application No. 135,315, Kasat, published Mar. 27, 1985.

Cream formulations, in general, have been less popular than other antiperspirant product forms. For example, some cream compositions may be sticky and produce aesthetically undesirable levels of residue on the skin. Creams may lso be "messy" and otherwise difficult to apply. Special packages and dispensers have been designed to reduce such application negatives. However, cream formulations known in the literature may be unacceptable for delivery from such dispensers.

It has been found that the antiperspirant creams of the present invention containing selected emollients and thickening materials have good application characteristics and very good efficacy while having good aesthetic and cosmetic characteristics. In particular, such compositions are stable, allowing use in cream dispensers. Such compositions also have good rheology during application, very good efficacy, and leave low levels of visible residue on the skin.

SUMMARY OF THE INVENTION

The present invention provides antiperspirant cream compositions, comprising:
  (a) from about 5% to about 60% of a volatile silicone oil;
  (b) from about 0.1% to about 60% of a non-volatile emollient having a viscosity of at least about 10 cs at 25° C.;
  (c) from about 2% to about 10% of a particulate thickening material; and
  (d) from about 15% to about 45% of a particulate antiperspirant active material; and
  (e) from about 0.1% to about 10% of a particulate hydrophilic polymer,
wherein said compositions have penetration force values of from about 150 g to about 800 g at 25° C. and at 50% relative humidity. These compositions preferably contain a cosmetic powder material, at a level of from about 2% to about 20%. This invention also provides methods for making these compositions.

DESCRIPTION OF THE INVENTION

The antiperspirant cream compositions of this invention contain five essential ingredients: a volatile silicone oil, a non-volatile emollient, a particulate thickening material, an antiperspirant active and a hydrophilic polymer. They may also contain certain optional components, such as (for example) cosmetic powders, colorants, perfumes and emulsifiers. The essential and optional components to be included in these creams must be "cosmetically acceptable", i.e., safe for human use and aesthetically acceptable at the levels encompassed by the present invention, at a reasonable risk/benefit ratio.

These compositions (herein "antiperspirant creams") encompass any semi-solid composition that is suitable for depositing antiperspirant material on human skin. The creams of this invention have a penetration force value of from about 150 grams (g) to about 800 g, preferably from about 200 g to about 550 g at 25° C. and at 50% relative humidity, as measured with a Stevens Texture Analyzer, manufactured by C. Stevens & Sons, Ltd. (This value is the force required to move a standardized 2 centimeter diameter disk through the product, for a distance of 15 millimeters, at a rate of 2 millimeters/second.)

In particular, the antiperspirant creams of this invention comprise:
  (a) from about 5% to about 60% of a volatile silicone oil;
  (b) from about 0.1% to about 60% of a non-volatile emollient having a viscosity of at least about 10 cs at 25° C.;
  (c) from about 2% to about 10% of a particulate thickening material; and
  (d) from about 15% to about 45% of a particulate antiperspirant active material; and
  (e) from about 0.1% to about 10% of a particulate hydrophilic polymer,
wherein said compositions have a penetration force value of from about 150 g to about 800 g at 25° C. and at 50% relative humidity. (As used herein, all percentages are by weight of total composition.)

Preferably, these creams contain from about 20% to about 60% off the volatile silicone oils, more preferably from about 30% to about 50%. The non-volatile emollient is preferably present at a level of from about 12% to about 30%, more preferably from about 15% to about 25%.

The particulate thickening material is preferably present at a level of from about 2% to about 7%, more preferably from about 2.8% to about 4.5%. The particulate hydrophilic polymer is preferably present at a level of from about 0.25% to about 5.0% and most preferably from about 1.0% to about 3.0%. Also preferably, the antiperspirant active material is present at a level of from about 20% to about 30%. The total level of all particulate materials (including the thickening material, the antiperspirant active material, and any optional materials in particulate form) is preferably from about 20% to about 50%, more preferably from about 30% to about 50%, more preferably from about 32% to about 40%. As used herein "particulate" materials are solid materials that are substantially insoluble in the volatile silicone oils and non-volatile emollients of the cream composition. The components of the invention are described in detail below.

Essential Components

Volatile Silicone Oil:

The antiperspirant compositions of this invention contain one or more volatile polyorganosiloxanes, which may function as a liquid emollient. (As used herein, "volatile" refers to those materials which have a measurable vapor pressure at ambient conditions.) The volatile polyorganosiloxanes useful herein may be cyclic or linear. A description of various volatile silicones is found in Todd, et al., "Volatile Silicone Fluids for Cosmetics", 91 *Cosmetics and Toiletries* 27–32 (1976), incorporated by reference herein.

Preferred cyclic silicones include polydimethylsiloxanes containing from about 3 to about 9 silicon atoms, preferably containing from about 4 to about 5 silicon atoms. Preferred linear silicone oils include the polydimethylsiloxanes containing from about 3 to about 9 silicon atoms. The linear volatile silicones generally have viscosities of less than about 5 centistokes at 25° C., while the cyclic materials have viscosities of less than about 10 centistokes. Examples of silicone oils useful in the present invention include: Dow Corning 344, Dow Corning 345, and Dow Corning 200 (manufactured by the Dow Corning Corporation); Silicone 7207 and Silicone 7158 (manufactured by the Union Carbide Corporation); SF1202 (manufactured by General Electric); and SWS-03314 (manufactured by Stouffer Chemical).

Non-volatile Emollient:

The present antiperspirant compositions contain a non-volatile emollient having a viscosity of at least about 10 centistokes (cs), at 25° C. The non-volatile emollient may consist of a single emollient, or a mixture having an overall viscosity of at least about 10 cs. Preferably, the non-volatile emollient has a viscosity of from about 100 cs to about 500 cs, more preferably from about 200 cs to about 500 cs.

Non-volatile emollients useful herein include fatty acid and fatty alcohol esters, nearly water-insoluble ethers and alcohols, polyorganosiloxanes, and mixtures thereof. Such emollients are described in 1 *Cosmetics, Science and Technology* 27–104 (M. Balsam and E. Sagarin ed. 1972), and U.S. Pat. No. 4,202,879, Shelton, issued May 13, 1980 (both incorporated by reference herein).

The present compositions preferably contain a non-volatile silicone oil as an emollient material. Such silicone oils include polyalkylsiloxanes, polyalkyarylsiloxanes, and polyethersiloxane copolymers. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation).

Particulate Thickening Material:

The compositions of this invention contain one or more materials which form a semi-solid cream formulation (as described above) with the other essential components. Such materials include colloidal silicas, silicates, and mixtures thereof. These materials preferably form a cream having a gel-like, shear-thinning matrix when used in the manner of this invention.

Silicates useful herein include, for example, montmorillonite clays and hydrophilically treated montmorillonites, e.g., bentonites, hectorites and colloidal magnesium silicates. When silicates are used as the thickening material of the present creams, they are preferably present at a level of from about 5% to abut 10%. Commercially-available silicates useful herein include, for example, the "Bentone" series of hydrophobic bentonites, manufactured by NL Industries, Inc.

When hydrophobically-treated bentonites are used as the thickening material, the creams of this invention also preferably contain a gel-promoting agent. Gel-promoting agents useful herein include, for example, water, lower alcohols (such as ethanol), acetone, propylene carbonate, and mixtures thereof. Such materials are preferably included at a level of from about 1% to about 3%, more preferably from about 1.5% to about 2.5%.

A preferred thickening material useful herein is finely divided silica, or "colloidal silica", which is comprised of micron to sub-micron sized silica particulates, with high surface areas (preferably greater than about 100 square meters per gram of material). Preferably, the colloidal silica material is less than about 1 micron in size. Also preferably, the silica material used in the present compositions is a fumed silica.

Fumed silicas can generally be described as fluffy, white, superfine powders of extremely low bulk density but having high surface areas. These fumed silicas are typically made by a vapor phase process that produces colloidal silica by the hydrolysis of silicon tetrachloride at a very high temperature. These materials typically consist of about 99.8% silicon dioxide by weight (on a moisture free basis), existing in three dimensional branched chain aggregates, with a surface that is hydrophilic and capable of hydrogen bonding. Such silicas have surface areas ranging from about 2.5 to about 1,200 square meters per gram. Colloidal silica materials are described in Hardy, et al., "The Use of Fumed Silica in Cosmetics", 2 *Cosmetic Technology* 35 (1980) (incorporated by reference herein) and R. Iler, *The Chemistry of Silica* (1979).

Colloidal silica materials among those useful herein are available from a variety of sources, including Syloid silicas (manufactured by Davison Chemical Division of W. R. Grace), Cab-O-Sil (manufactured by Cabot Corporation), and Aerosil (manufactured by Degussa A. G.). Cab-O-Sil is a preferred commercially available colloidal silica useful herein, with a surface area ranging from about 200 to about 400 square meters per gram.

Particulate Antiperspirnt Material:

The particulate antiperspirant materials of this invention comprise any compound or composition or mixtures thereof, having antiperspirant activity. Astringent metallic salts are preferred antiperspirant materials for use herein, particularly including the inorganic and organic salts of aluminum, zirconium and zinc, and mixtures thereof. Particularly preferred are the aluminum and zirconium salts such as aluminum halides, aluminum hydroxy halides, zirconyl oxide halides, zirconyl hydroxy halides, and mixtures thereof.

Preferred aluminum salts include those of the formula

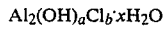

$$Al_2(OH)_aCl_b \cdot xH_2O$$

wherein a is from about 2 to about 5; a+b=6; x is from about 1 to about 6; and wherein a, b, and x may have non-integer values. Particularly preferred are aluminum chlorhydroxides referred to as "5/6 basic chlorhydroxide", wherein a=5, and "⅔ basic chlorhydroxide," wherein a=4. Processes for preparing aluminum salts are disclosed in the following documents, all incorporated by reference herein: U.S. Pat. No. 3,887,692, Gilman, issued June 3, 1975; U.S. Pat. No. 3,904,741, Jones et al., issued Sept. 9, 1975; U.S. Pat. No. 4,359,456, Gosling, et al., issued Nov. 16, 1982; and British patent specification No. 2,048,229, Fitzgerald, et al., published Dec. 10, 1980. Mixtures of aluminum salts are described in British patent specification No. 1,347,950, Shin, et al., published Feb. 27, 1974 (incorporated by reference herein).

Zirconium salts are also preferred for use in antiperspirant creams of the present invention. Such salts are of the general formula

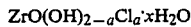

$$ZrO(OH)_{2-a}Cl_a \cdot xH_2O$$

wherein a is from about 1.5 to about 1.87; x is from about 1 to about 7; and wherein a and n may have non-integer values. These zirconium salts are disclosed in Belgium Pat. No. 825,146, Schmitz, issued Aug. 4, 1975, (incorporated by reference herein). Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in U.S. Pat. No. 3,679,068, Lueddes, et al., issued Feb. 12, 1974 (incorporated herein by reference), and U.S. Pat. No. 4,120,948, Shelton, issued Oct. 17, 1978 (incorporated by reference herein).

Also useful are the ZAG complexes disclosed in G.P. patent application No. 2,144,992, Callaghan et al., published Mar. 20, 1985. These ZAG actives, when analyzed by high pressure gel permeation chromatography, exhibit a distribution pattern having four or more successive peaks or "bands" where the height ratio of Bands IV to III is greater than 2:1.

More preferred are ZAG actives which have a total area under the curve of bands I and II of less than about 10%, preferably less than about 5%, more preferably less than about 2% and most preferably less than about 1%.

Hydrophilic Polymers:

The antiperspirant cream compositions of the present invention comprise at least one particulate hydrophilic polymer. The inclusion of the hydrophilic polymer assists in removal of the antiperspirant residue by washing. Preferred hydrophilic polymers include cellulose ether polymers (cationic, neutral, and anionic), modified starches, polyamides, (especially polyacrylamides), and polypeptides, as disclosed generally in Davidson, *Handbook of Water-Soluble Gums and Resins,* 1980. Preferably, the polymer is selected from non-ionic cellulose ether polymers. Such cellulose ether polymers are disclosed in Davidson, supra, Chapters 4 and 12-13. More preferred are cellulose ether polymers selected from alkylcelluloses (e.g., methylcellulose), hydroxyalkylalkylcelluloses (e.g., hydroxypropylmethylcellulose; hydroxybutylmethylcellulose; hydroxyethylmethylcellulose; ethylhydroxyethylcellulose), hydroxyalkylcelluloses (e.g., hydroxyethylcellulose; hydroxypropylcellulose), and mixtures thereof. Most preferred are hydroxyalkylcelluloses, especially hydroxyethylcellulose and hydroxy propylcellulose. The cellulose ether polymers typically have molecular weights within the range of from about 20,000 to about 5,000,000 and more typically within the range of from about 50,000 to about 500,000. Cellulose ether polymers are described in "Handbook of Water-Soluble Gums and Resins" (McGraw-Hill Book Co., N.Y.; 1980; Davidson, editor), Chapters 3, 4, 12 and 13, the disclosures of which are incorporated herein by reference in their entirety.

The cellulose ether polymers to be utilized herein bind to polar solvents such as water and ethanol. However, as utilized in the antiperspirant compositions herein, these polymers are exposed to very little if any polar solvents. Furthermore, the cellulose ether polymers utilized herein are not dissolved in the antiperspirant composition but rather are distributed throughout the composition in particulate form. It is preferred that the particle size be small to prevent the antiperspirant composition from having a "gritty" feel. Preferably, the particle size is from 1 to about 500 microns, more preferably from about 1 to about 100 microns, and mst preferably from about 15 to about 75 microns. In the case of non-spherical particles, the longest dimension of the particles is considered for these preferred limits.

Representative examples of preferred cellulose ether polymers useful in the compositions of the present invention are: hydroxyethylcellulose (Natrosol 250M sold by Hercules Chemical Co.); hydroxypropylcellulose (Klucel sold by Hercules Chemical Co.); methyl cellulose (Methocel-A supplied by Dow Chemical Co.); and poly(ethylene oxide) (Polyox sold by Union Carbide Corp.). Most preferred is hydroxyethylcellulose.

The hydrophilic polymers in total typically comprise from about 0.1% to about 10% by weight of the compositions of the present invention, more preferably from about 0.25% to about 5%, and most preferably from about 1% to about 3%.

Non-essential Components

The compositions of the present invention may also contain optional components which modify the physical characteristics of the vehicles, or serve as "active" components when deposited on the skin in addition to the particulate antiperspirant material. Additional active components include bacteriostats and fungistats. The particular non-active components that may be useful will depend upon the form of application that is desired. Such components include, for example, emollients, colorants, perfumes, powders, and emulsifiers. Optional components useful herein are described in the following documents, all incorporated by reference herein: U.S. Pat. No. 4,049,792, Elsnau, issued Sept. 20, 1977; Canadian Pat. No. 1,164,347, Beckmeyer, et al., issued Mar. 27, 1984; European patent specitication No. 117,070, May, published Aug. 29, 1984; and Geria, "Formulation of Stick Antiperspirants and Deodorants," 99 *Cosmetics & Toiletries* 55-60 (1984).

A preferred optional component is a cosmetic powder (or mixture of powders), incorporated at a level of from about 2% to about 20%, preferably from about 2% to about 10%. Preferred cosmetic powders useful herein include "inert spherical particulate materials" having a mean diameter of at least about 10 microns.

The "spherical particulate materials" are preferably essentially free of (i.e., containing less than 2% by weight of material) particulates having diameters greater than about 150 microns. Also preferably, the particles have a mean diameter of from about 15 microns to about 75 microns. Commercially-available inert particulate materials among those useful herein may be of a non-uniform size distribution, containing some particles outside the size ranges described herein. For the purposes of this invention, such non-uniform materials preferably have a mean diameter within the ranges described above.

Particularly preferred for use in the present invention is the inclusion of the inert spherical particulate materials in a ratio of particulate hydrophilic polymer to spherical particulate materials of from about 10:1 to about 1:10, preferably 5:1 to about 1:5.

As referred to herein, "inert particulates" are those particulates comprised of materials or mixtures of materials that are essentially water insoluble and which neither melt nor decompose nor react with the wax thickener materials, silicone oils or other components of the antiperspirant sticks, under the conditions of preparation and of use. Among the optional particulate materials that may be incorporated in this invention include those comprised of polyolefins (such as polystyrene, polyethylene, and polypropylene), nylon, waxes, Teflon®, insoluble cross-linked starches, and mixtures thereof.

Preferred inert particulate materials include those comprised of polyolefins, particularly polyethylene. Without being limited by theory, it is believed that these materials enhance the stability of the antiperspirant cream matrix by adding support to the matrix formed by the particulate thickening material. Polyethylene materials, as well as particulates made from other polyolefins, can be prepared by any of several methods known in the art. (See, e.g., U.S. Pat. No. 2,825,721, Hogan, et al., issued Mar. 4, 1958.) Polyethylene polymers with low molecular weights such as 1,500 to 3,000, as well as polymers of such high molecular weights as 35,000 to 100,000, may be used. One such polyethylene powder useful in this invention is Microthene ®, manufactured by U.S.I. Chemicals, having a mean particle diameter of from about 14 to about 20 microns. Among other commercially-available materials useful herein are 3M Glass Bubbles (soda-lime borosilicate glass spheres sold by 3M Company) and Miralite ® (low density polyvinylidene chloride hollow microspheres, of approximately 30 microns mean diameter, sold by Pierce & Stevens Chemical Corporation).

Other cosmetic powders useful herein include silicate powders (including talc, aluminum silicate, and magnesium silicate), modified corn starches, metallic stearates, and mixtures thereof. Talc is described in K. S. Plotkin, "Cosmetic Talc" 11 *C.T.F.A. Cosmetic Journal* 13–16 (1979), incorporated by reference herein. Commercially-available powders include, for example, Veecote (anhydrous aluminum silicate, sold by R. T. Vanderbilt Company, Inc.) and Dry Flo (aluminum starch succinate, sold by National Starch and Chemicals Company).

Methods

A preferred method for making the antiperspirant creams of this invention generally comprises the steps of:

(a) admixing the essential and optional components of said creams, under low-shear conditions, yielding a liquid mixture having a penetration value of from about 15 grams to about 200 grams at 25° C. and at 50% relative humidity; and (b) milling said liquid mixture, under high shear conditions, with a dispersing disc at a disc tip speed of at least about 9 meters/second.

These processes may be batch processes (i.e., involving discrete processing steps) or continuous (i.e., wherein the product composition is passed between processing steps in essentially continuous increments). The equipment used in this preferred process is commercially available.

The admixing step preferably involves first admixing the volatile silicone oil and non-volatile emollient and any other liquid components. The thickening material is then added, followed by the antiperspirant active material and particulate hydrophilic polymer and any other particulate components. Conventional blending equipment may be used. Preferably the penetration value of the mixture is from about 40 g to about 175 g at 25° C. and a 50% relative humidity.

The high-shear milling step is preferably performed in a conventional dispersing disc milling apparatus. The tip speed of the dispersing disc is preferably from about 18 meters/second to about 22 meters/second. The mixture is preferably milled until a maximum penetration value is obtained, preferably at least about 200 g, preferably from about 300 g to about 400 g at 25° C. and at 50% relative humidity.

Creams of this invention may be packed in conventional antiperspirant cream containers, known in the art. Such packages typically contain the cream in bulk form. The cream is then applied by hand, or by a pad or similar applicator device. However, the present creams may also be provided in other package dispensers, designed to extrude or otherwise directly apply the creams to the skin.

The following non-limiting examples illustrate the compositions, processes nd uses of the present invention.

EXAMPLE I

An antiperspirant cream, according to this invention, was made comprising:

| Component | % (by weight) |
| --- | --- |
| cyclomethicone (d5) | 43.5 |
| dimethicone (350 cs) | 20.0 |
| Cab-O-Sil HS-5[1] | 4.0 |
| Microthene FN510[2] | 3.0 |
| Natrosol[3] | 2.0 |
| Reach AZ[4] | 26.7 |
| fragrance | 0.8 |

[1] colloidal silica thickening material, sold by Cabot Corporation.
[2] low density polyethylene powder, sold by U.S.I. Chemicals.
[3] hydroxy ethyl cellulose, sold by Hercules, Inc.
[4] zirconium-aluminum-glycine hydroxychloride complex, particulate antiperspirant active material, sold by Reheis Chemical Company.

The cyclomethicone and dimethicone and perfume are added to a stainless steel mixing vessel. The Cab-O-Sil is then added, followed by the Microthene and Natrosol and, finally, the antiperspirant active. The composition is thoroughly stirred after addition of each particulate material.

The composition is then milled, using a Black & Decker Die Grinder (Model 4420, type 4) with a 6.35 cm diameter Cowles dispersing blade at approximately 6000 rpm, for approximately 5 minutes. The penetration force value of the milled composition is approximately 300 grams at 25° C. and at 50% relative humidity.

An antiperspirant cream formulation, comprised as above, is applied to the underarm area of a human subject, and reduces the perspiration in the applied area.

EXAMPLE II

An antiperspirant cream, according to this invention, is made comprising:

| Component | % (by weight) |
|---|---|
| cyclomethicone (d5) | 43.5 |
| dimethicone (350 cs) | 20.0 |
| Cab-O-Sil HS-5[1] | 4.0 |
| Microthene FN510[2] | 3.0 |
| polyox[3] | 2.0 |
| Reach AZ[4] | 26.7 |
| fragrance | 0.8 |

[1]colloidal silica thickening material, sold by Cabot Corporation.
[2]low density polyethylene powder sold by U.S.I. Chemicals.
[3]poly (ethylene oxide), sold by Union Carbide Corp.
[4]zirconium-aluminum-glycine hydroxychloride complex, particulate antiperspirant active material, sold by Reheis Chemical Company The cyclomethicone and dimethicone and perfume are added to a stainless steel mixing vessel. The Cab-O-Sil is then added, followed by the Microthene and, finally, the antiperspirant active. The composition is thoroughly stirred after addition of each particulate material.

The composition is then milled, using a Black & Decker Die Grinder (Model 4420, type 4) with a 6.35 cm diameter Cowles dispersing blade at approximately 6000 rpm, for approximately 5 minutes. The penetration force value of the milled composition is to be approximately 300 grams at 25° C. and at 50% relative humidity.

An antiperspirant cream formulation, comprised as above, is applied to the underarm area of a human subject, and reduced the perspiration in the applied area.

EXAMPLE III

An antiperspirant cream, according to this invention, is made comprising:

| Component | % (by weight) |
|---|---|
| cyclomethicone (d5) | 44.3 |
| dimethicone (350 cs) | 15.0 |
| Cab-O-Sil | 4.0 |
| Natrosol | 2.0 |
| Microthene | 3.0 |
| talc | 5.0 |
| ZAG antiperspirant active | 26.7 |

The antiperspirant cream is made by a method analogous to that described in Example I. The penetration force value is approximately 520 at 25° C. and at 50% relative humidity.

EXAMPLE IV

An antiperspirant cream, according to this invention, is made comprising:

| Component | % (by weight) |
|---|---|
| cyclomethicone (D4) | 45.3 |
| dimethicone (350 cs) | 20.0 |
| Cab-O-Sil | 3.0 |
| Natrosol | 2.0 |
| Microthene | 3.0 |
| ZAG antiperspirant active | 26.7 |

The antiperspirant cream is made by a method analogous to that described in Example I. The penetration force value is approximately 170 at 25° C. and at 50% relative humidity.

EXAMPLE V

An antiperspirant cream, according to this invention, is made comprising:

| Component | % (by weight) |
|---|---|
| cyclomethicone (D4) | 34.3 |
| dimethicone (350 cs) | 20.0 |
| Cab-O-Sil | 4.0 |
| Natrosol | 3.0 |
| Microthene | 12.0 |
| ZAG antiperspirant active | 26.7 |

The antiperspirant cream is made by a method analogous to that described in Example I. The penetration force value is approximately 750 at 250° C. and at 50% relative humidity.

EXAMPLE VI

An antiperspirant cream, according to this invention, is made comprising:

| Component | % (by weight) |
|---|---|
| cyclomethicone (D5) | 39.8 |
| dimethicone (10 cs) | 10.0 |
| Bentone 38[1] | 3.0 |
| Cab-O-Sil | 2.0 |
| Natrosol | 2.0 |
| Microthene | 6.0 |
| talc | 5.0 |
| Veecote[2] | 4.5 |
| ZAG antiperspirant active | 26.7 |

[1]hydrophobically-treated bentonite, manufactured by NL Industries, Inc.
[2]anhydrous aluminum silicate, manufactured by R. T. Vanderbilt Company The antiperspirant cream is made by a method analogous to that described in Example I. The penetration force value is approximately 350 at 25° C. and at 50% relative humidity.

What is claimed is:

1. An antiperspirant cream composition, comprising:
   (a) from about 5% to about 60% of a volatile silicone oil;
   (b) from about 0.1% to about 60% of a non-volatile emollient having a viscosity of at least about 10 cs at 25° C.;
   (c) from about 2% to about 10% of a particulate thickening material;
   (d) from about 15% to about 45% of a particulate antiperspirant active material; and
   (e) from about 0.25% to about 5% of a particulate hydrophilic polymer selected from the group consisting of cellulose ether polymers, polyamides, polypeptides, and mixtures thereof;
   wherein said composition has a penetration force value of from about 150 g to about 800 g at 25° C. and 50% relative humidity.

2. An antiperspirant cream composition, according to claim 1, wherein said composition has a penetration force value of from about 200 g to about 550 g at 250° C. and at 50% relative humidity.

3. An antiperspirant cream composition, according to claim 2, wherein said composition has a total level of particulate of from about 20% to about 50%.

4. An antiperspirant cream composition, according to claim 3, wherein said volatile silicone oil is present at a level of from about 30% to about 50%.

5. An antiperspirant cream composition, according to claim 4, wherein said non-volatile emollient is present at a level of from about 15% to about 25%.

6. An antiperspirant cream composition, according to claim 5, wherein said non-volatile emollient has a viscosity of from about 100 cs to about 500 cs.

7. An antiperspirant cream composition, according to claim 6, wherein said non-volatile emollient is a polyorganosiloxane.

8. An antiperspirant cream according to claim 7 wherein said hydrophilic polymer is a cellulose ether polymer.

9. An antiperspirant cream according to claim 8 wherein said cellulose ether polymer is selected from the group consisting of hydroxyethyl cellulose, hydroxypropyl cellulose and mixtures thereof.

10. An antiperspirant cream composition, according to claim 7, additionally comprising from about 2% to about 20% of a cosmetic powder material.

11. An antiperspirant cream composition, according to claim 10, wherein said cosmetic powder material is a spherical particulate material and is present at a level of from about 2% to about 10%.

12. An antiperspirant cream according to claim 11, wherein the ratio of hydrophilic polymer to spherical particulate materials is from about 1:5 to about 5:1.

13. An antiperspirnt cream according to claim 12, wherein said hydrophilic polymer is a cellulose ether polymer.

14. An antiperspirant cream according to claim 13, wherein said cellulose ether polymer is selected from the group consisting of hydroxyethyl cellulose, hydroxypropyl cellulose, and mixtures thereof.

15. An antiperspirant cream composition, according to claim 7, wherein said particulate thickening material is a colloidal silica.

16. An antiperspirant cream composition, according to claim 15 wherein said colloidal silica is present at a level of from about 2.8% to about 4.5%.

17. An antiperspirant cream composition, according to claim 14, wherein said particulate thickening material is a silicate.

18. An antiperspirant cream composition, according to claim 17 additionally comprising a gel-promoting agent.

19. An antiperspirant cream composition, according to claim 18 wherein said silicate is present at a level of from about 5% to about 10%.

20. An antiperspirant cream according to claim 7 wherein said particulate antiperspirant active material is a zirconium aluminum glycine complex.

21. An antiperspirant cream according to claim 20 wherein said zirconium aluminum glycine complex has a high pressure gel permeation chromatography distribution pattern having four or more successive bands wherein the total area under the curve of the first two bands is less than about 2%.

22. An antiperspirant cream according to claim 12 wherein said particulate antiperspirant active material is a zirconium aluminum glycine complex.

23. An antiperspirant cream according to claim 21 wherein said zirconium aluminum glycine complex has a high pressure gel permeation chromatography distribution pattern having four or more successive bands wherein the total area under the curve of the first two bands is less than about 2%.

24. A method for making an antiperspirant cream composition of claim 1, comprising the steps of:
(a) admixing said volatile silicone oil, said non-volatile emollient, said particulate thickening material and said particulate antiperspirant active, under low-shear conditions, to form a liquid composition having a penetration force value of from about 15 g to about 200 g at 25° C. and at 50% relative humidity; and
(b) milling said liquid mixture, under high shear conditions using a dispersing disk at a disc tip speed of at least about 9 meters/second.

* * * * *

UNITED STATES PATENT AND TRADEMARK OFFICE
CERTIFICATE OF CORRECTION

PATENT NO. : 4,853,214

DATED : August 1, 1989

INVENTOR(S) : Thomas V. Orr

It is certified that error appears in the above-identified patent and that said Letters Patent is hereby corrected as shown below:

In Claim 2, column 10, line 64, "250°" should read -- 25° --.

In column 10, line 21 "250°" should read -- 25° --.

Signed and Sealed this

Seventeenth Day of September, 1991

Attest:

HARRY F. MANBECK, JR.

Attesting Officer

Commissioner of Patents and Trademarks